(12) United States Patent
Gong et al.

(10) Patent No.: US 11,013,695 B2
(45) Date of Patent: May 25, 2021

(54) NANOCAPSULE DELIVERY SYSTEM FOR RIBONUCLEOPROTEINS

(71) Applicant: Wisconsin Alumni Research Foundation, Madison, WI (US)

(72) Inventors: Shaoqin Gong, Middleton, WI (US); Amr Abdeen, Madison, WI (US); Krishanu Saha, Madison, WI (US); Guojun Chen, Madison, WI (US); Yuyuan Wang, Madison, WI (US); Ruosen Xie, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 456 days.

(21) Appl. No.: 16/113,963

(22) Filed: Aug. 27, 2018

(65) Prior Publication Data
US 2019/0099381 A1 Apr. 4, 2019

Related U.S. Application Data

(60) Provisional application No. 62/551,202, filed on Aug. 28, 2017.

(51) Int. Cl.
| | |
|---|---|
| A61K 9/51 | (2006.01) |
| A61K 48/00 | (2006.01) |
| A61K 47/32 | (2006.01) |
| C12N 15/11 | (2006.01) |
| A61K 38/46 | (2006.01) |
| C12N 15/113 | (2010.01) |
| A61K 31/7105 | (2006.01) |
| A61K 9/50 | (2006.01) |
| C12N 9/22 | (2006.01) |
| C12N 15/90 | (2006.01) |

(52) U.S. Cl.
CPC ............ *A61K 9/51* (2013.01); *A61K 9/5026* (2013.01); *A61K 9/5138* (2013.01); *A61K 31/7105* (2013.01); *A61K 38/46* (2013.01); *A61K 47/32* (2013.01); *A61K 48/0041* (2013.01); *A61K 48/0091* (2013.01); *C12N 9/22* (2013.01); *C12N 15/11* (2013.01); *C12N 15/111* (2013.01); *C12N 15/113* (2013.01); *C12N 15/907* (2013.01); *C12N 2310/20* (2017.05); *C12N 2320/32* (2013.01); *C12N 2800/80* (2013.01)

(58) Field of Classification Search
CPC ...................................................... A61K 9/51
See application file for complete search history.

(56) References Cited

U.S. PATENT DOCUMENTS 7,687,600 B2 * 3/2010 Thayumanavan .... C07C 237/22
528/480

FOREIGN PATENT DOCUMENTS

| WO | WO-2015/089462 | 6/2015 |
| WO | WO-2016/183402 | 11/2016 |

OTHER PUBLICATIONS

Yuyuan Wang. PhD disseratation 2019. University of Wisconson—Madison. "Multifunctional Nanoplatforms for the Delivery of CRISPR/Cas9-Based Genome Editing Machinery." (Year: 2019).*
Chen et al., Tumor-targeted pH/redox dual-sensitive unimolecular nanoparticles for efficient siRNA delivery, Journal of Controlled Release, vol. 259, Aug. 10, 2017, pp. 105-114.

* cited by examiner

*Primary Examiner* — Scott Long
(74) *Attorney, Agent, or Firm* — Foley & Lardner LLP

(57) ABSTRACT

Provided herein are nanocapsules comprising a single ribonucleoprotein (RNP) complex as a core and an biodegradable crosslinked polymer shell that encapsulates the core, wherein the RNP complex comprises a Cas9 polypeptide and a guide RNA, and the biodegradable crosslinked polymer shell comprises polymerized monomers of imidazolyl acryloyl monomers, bisacryloyl disulfide monomers (a biodegradable cross-linker), optionally PEG acryloyl monomers, and either cationic acryloyl monomers, anionic acryloyl monomers, or both cationic and anionic acryloyl monomers (optionally in combination with non-ionic acryloyl monomers) as defined herein. Also provided are methods of making the nanocapsules, kits containing the nanocapsules and methods of delivering the encapsulated RNP to cells.

30 Claims, 8 Drawing Sheets
Specification includes a Sequence Listing.

FIG. 4B
FIG. 4C
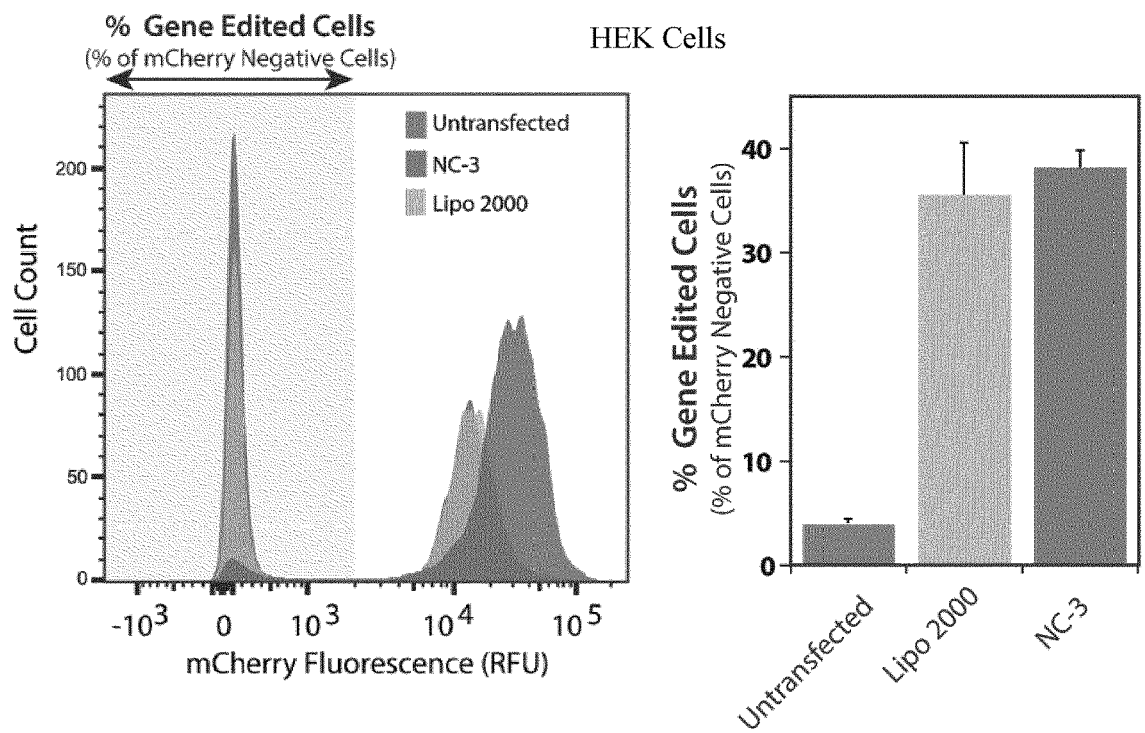
FIG. 4D
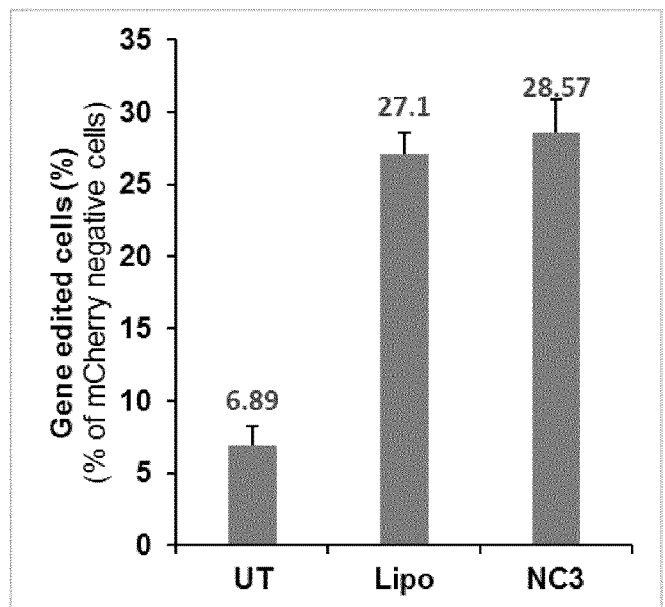

FIG. 5A
FIG. 5B
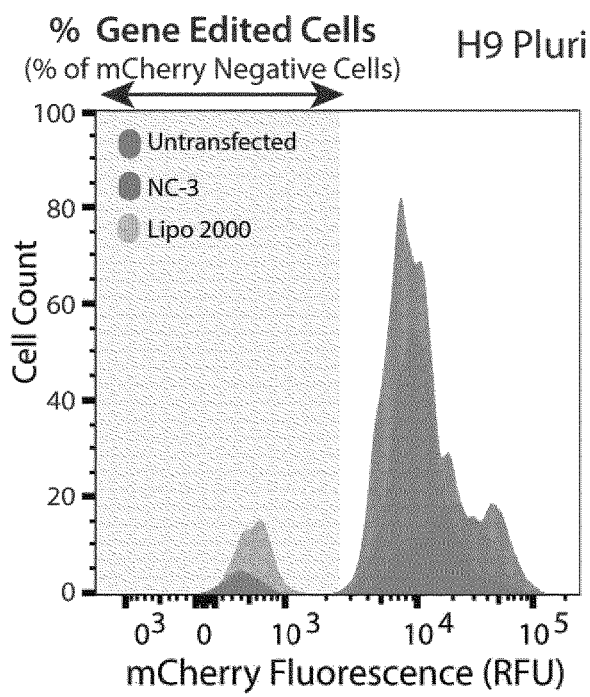
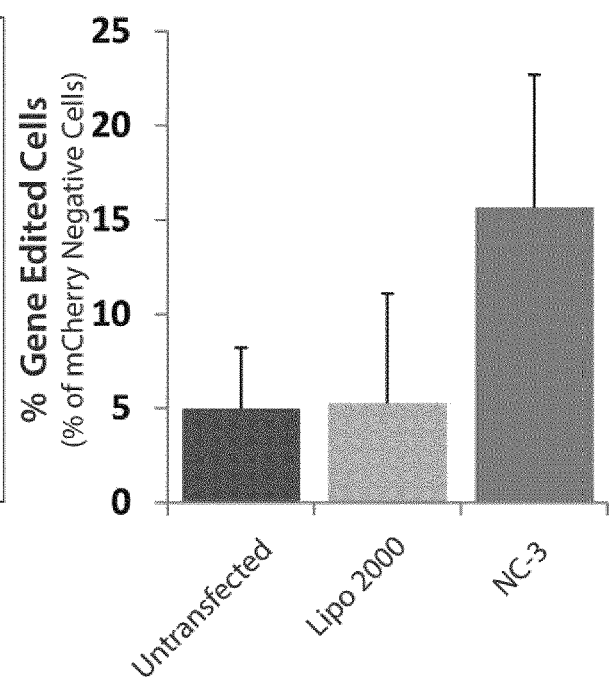

FIG. 6A
FIG. 6B
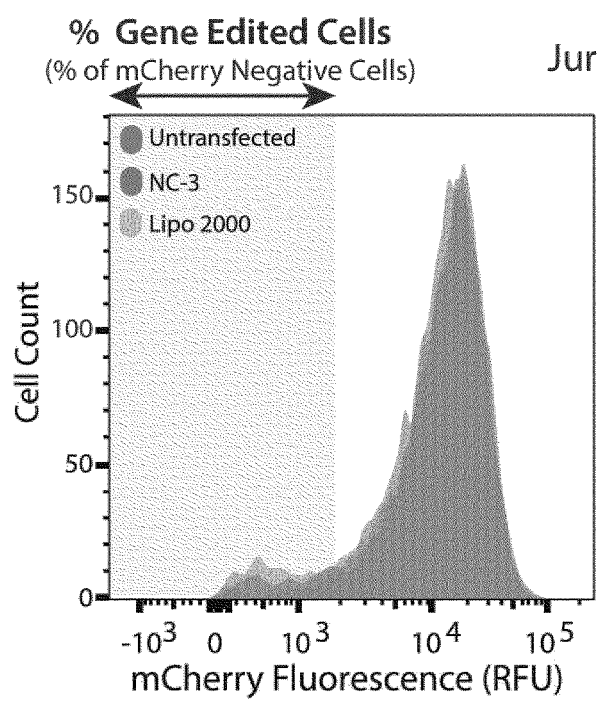
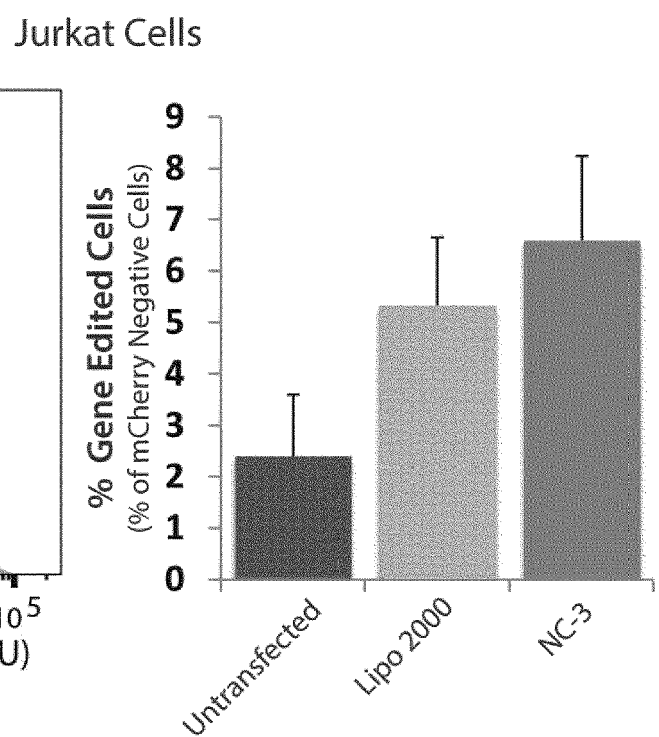

NC-3

PBS

Low mag

High mag

SEQUENCE LISTING

<160> NUMBER OF SEQ ID NOS: 47

<210> SEQ ID NO 1
<211> LENGTH: 180
<212> TYPE: RNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 1
nnnnnnnnnn nnnnnnnnnn guuuaagagc uaugcugcga auacgagaug cggccgccga    60
ccagaaucau gcaagugcgu aagauagucg cgggucggcg gcucguauuc gcagcauagc   120
aaguuuaaau aaggcuaguc cguuaucaac uugaaaaagu ggcaccgagu cggugcuuuu   180

<210> SEQ ID NO 2
<211> LENGTH: 184
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 2
nnnnnnnnnn nnnnnnnnnn guuuaagagc uaugcuggaa acagcauagc aaguuuaaau    60
aaggcuaguc cguuaucaac uucgaauacg agaugcggcc gccgaccaga aucaugcaag   120
ugcguaagau agucgcgggu cggcggcucg uauucggaaa aguggcaccg agucggugc   180 uuuu                                                                184

<210> SEQ ID NO 3
<211> LENGTH: 184
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 3
nnnnnnnnnn nnnnnnnnnn guuuaagagc uaugcuggaa acagcauagc aaguuuaaau    60
aaggcuaguc cguuaucaac uugaaaaagu ggcaccgagu cggugccgaa uacgagaugc   120
ggccgccgac cagaaucaug caagugcgua agauagucgc gggucggcgg cucguauucg   180
uuuu                                                                184

<210> SEQ ID NO 4
<211> LENGTH: 12
<212> TYPE: PRT
<213> ORGANISM: Human immunodeficiency virus

<400> SEQUENCE: 4

Gly Arg Lys Lys Arg Arg Gln Arg Arg Arg Pro Gln
 1               5                  10

<210> SEQ ID NO 5
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Lys Leu Ala Leu Lys Leu Ala Leu Lys Ala Leu Lys Ala Ala Leu Lys
1               5                   10                  15

Leu Ala

<210> SEQ ID NO 6
<211> LENGTH: 15
<212> TYPE: PRT
<213> ORGANISM: Drosophila sp.

<400> SEQUENCE: 6

Arg Gln Ile Lys Trp Phe Gln Asn Arg Arg Met Lys Trp Lys Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gln Ile Arg Ile Trp Phe Gln Asn Arg Arg Met Arg Trp Arg Arg
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Ser Ile Pro Pro Glu Val Lys Phe Asn Lys Pro Phe Val Tyr Leu
1               5                   10                  15

Ile

<210> SEQ ID NO 9
<211> LENGTH: 13
<212> TYPE: PRT
<213> ORGANISM: Rana temporaria

<400> SEQUENCE: 9

Phe Val Gln Trp Phe Ser Lys Phe Leu Gly Arg Ile Leu
1               5                   10

<210> SEQ ID NO 10
<211> LENGTH: 10
<212> TYPE: PRT
<213> ORGANISM: Maurus palmatus

<400> SEQUENCE: 10

Gly Asp Cys Leu Pro His Leu Lys Leu Cys
1               5                   10

<210> SEQ ID NO 11
<211> LENGTH: 18
<212> TYPE: PRT
<213> ORGANISM: Mus sp.
```

```
<400> SEQUENCE: 11

Leu Leu Ile Ile Leu Arg Arg Arg Ile Arg Lys Gln Ala His Ala His
1               5                   10                  15

Ser Lys

<210> SEQ ID NO 12
<211> LENGTH: 24
<212> TYPE: PRT
<213> ORGANISM: Homo sapiens

<400> SEQUENCE: 12

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 13
<211> LENGTH: 30
<212> TYPE: PRT
<213> ORGANISM: Unknown
<220> FEATURE:
<223> OTHER INFORMATION: Description of Unknown:
      Neurturin sequence

<400> SEQUENCE: 13

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30

<210> SEQ ID NO 14
<211> LENGTH: 18
<212> TYPE: PRT
<213> ORGANISM: Drosophila sp.

<400> SEQUENCE: 14

Arg Gln Ile Lys Ile Trp Phe Gln Asn Arg Arg Met Lys Trp Lys Lys
1               5                   10                  15

Gly Gly

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30

<210> SEQ ID NO 16
<211> LENGTH: 11
<212> TYPE: PRT
<213> ORGANISM: Human immunodeficiency virus

<400> SEQUENCE: 16

Tyr Gly Arg Lys Lys Arg Arg Gln Arg Arg
1               5                   10
```

```
<210> SEQ ID NO 17
<211> LENGTH: 18
<212> TYPE: PRT
<213> ORGANISM: Unknown
<220> FEATURE:
<223> OTHER INFORMATION: Description of Unknown:
      SynB1 sequence

<400> SEQUENCE: 17

Arg Gly Gly Arg Leu Ser Tyr Ser Arg Arg Arg Phe Ser Thr Ser Thr
1               5                   10                  15

Gly Arg

<210> SEQ ID NO 18
<211> LENGTH: 10
<212> TYPE: PRT
<213> ORGANISM: Unknown
<220> FEATURE:
<223> OTHER INFORMATION: Description of Unknown:
      SynB3 sequence

<400> SEQUENCE: 18

Arg Arg Leu Ser Tyr Ser Arg Arg Arg Phe
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Ile Arg Arg Arg Lys Lys Leu Arg Arg Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Gln Arg Arg Thr Ser Lys Leu Met Lys Arg
1               5                   10

<210> SEQ ID NO 21
<211> LENGTH: 15
<212> TYPE: PRT
<213> ORGANISM: Flock house virus

<400> SEQUENCE: 21

Arg Arg Arg Arg Asn Arg Thr Arg Arg Asn Arg Arg Arg Val Arg
1               5                   10                  15

<210> SEQ ID NO 22
<211> LENGTH: 19
<212> TYPE: PRT
<213> ORGANISM: Brome mosaic virus

<400> SEQUENCE: 22

Lys Met Thr Arg Ala Gln Arg Arg Ala Ala Ala Arg Arg Asn Arg Trp
```

Thr Ala Arg

<210> SEQ ID NO 23
<211> LENGTH: 13
<212> TYPE: PRT
<213> ORGANISM: Human T-cell leukemia virus II

<400> SEQUENCE: 23

Thr Arg Arg Gln Arg Thr Arg Arg Ala Arg Arg Asn Arg
1               5                   10

<210> SEQ ID NO 24
<211> LENGTH: 13
<212> TYPE: PRT
<213> ORGANISM: Human immunodeficiency virus

<400> SEQUENCE: 24

Gly Arg Lys Lys Arg Arg Gln Arg Arg Arg Pro Pro Gln
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Arg Arg Arg Arg Arg Arg Arg Arg Arg Pro Pro Gln
1               5                   10

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Leu Ala Leu Lys Leu Ala Leu Lys Leu Ala Leu Ala Leu Lys Leu
1               5                   10                  15

Ala

<210> SEQ ID NO 28
<211> LENGTH: 27
<212> TYPE: PRT
<213> ORGANISM: Homo sapiens

```
<400> SEQUENCE: 28

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 29
<211> LENGTH: 27
<212> TYPE: PRT
<213> ORGANISM: Unknown
<220> FEATURE:
<223> OTHER INFORMATION: Description of Unknown:
      FBP sequence

<400> SEQUENCE: 29

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 31
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 33
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 34

Arg Arg Arg Arg Arg Arg Arg Arg Arg Arg Arg Arg Arg Arg Arg Arg
1               5                   10                  15

Arg

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 35

Lys Lys Lys Lys Lys Lys Lys Lys Lys Lys Lys Lys Lys Lys Lys Lys
1               5                   10                  15

Lys

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminocaproic acid
<220> FEATURE:
<221> NAME/KEY: MOD_RES
<222> LOCATION: (4)..(4)
<223> OTHER INFORMATION: Aminocaproic acid
<220> FEATURE:
<221> NAME/KEY: MOD_RES
<222> LOCATION: (6)..(6)
<223> OTHER INFORMATION: Aminocaproic acid
<220> FEATURE:
<221> NAME/KEY: MOD_RES
<222> LOCATION: (8)..(8)
<223> OTHER INFORMATION: Aminocaproic acid
<220> FEATURE:
```

```
<221> NAME/KEY: MOD_RES
<222> LOCATION: (10)..(10)
<223> OTHER INFORMATION: Aminocaproic acid
<220> FEATURE:
<221> NAME/KEY: MOD_RES
<222> LOCATION: (12)..(12)
<223> OTHER INFORMATION: Aminocaproic acid

<400> SEQUENCE: 36

Arg Xaa Arg Xaa Arg Xaa Arg Xaa Arg Xaa Arg Xaa Arg
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (4)..(4)
<223> OTHER INFORMATION: Aminobutyric acid
<220> FEATURE:
<221> NAME/KEY: MOD_RES
<222> LOCATION: (6)..(6)
<223> OTHER INFORMATION: Aminobutyric acid
<220> FEATURE:
<221> NAME/KEY: MOD_RES
<222> LOCATION: (8)..(8)
<223> OTHER INFORMATION: Aminobutyric acid
<220> FEATURE:
<221> NAME/KEY: MOD_RES
<222> LOCATION: (10)..(10)
<223> OTHER INFORMATION: Aminobutyric acid
<220> FEATURE:
<221> NAME/KEY: MOD_RES
<222> LOCATION: (12)..(12)
<223> OTHER INFORMATION: Aminobutyric acid

<400> SEQUENCE: 37

Arg Xaa Arg Xaa Arg Xaa Arg Xaa Arg Xaa Arg Xaa Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Gly Arg Gly Arg Gly Arg Gly Arg Gly Arg Gly Arg
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Met Arg Met Arg Met Arg Met Arg Met Arg Met Arg
1               5                   10
```

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Thr Arg Thr Arg Thr Arg Thr Arg Thr Arg Thr Arg
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Arg Ser Arg Ser Arg Ser Arg Ser Arg Ser Arg
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Arg Arg Arg Arg Arg Arg Arg Arg
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ala Arg Ala Arg Ala Arg Ala Arg Ala Arg Ala Arg
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Arg Arg Arg Arg Arg Arg
1               5

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Cys Tyr Gly Arg Lys Lys Arg Arg Gln Arg Arg Arg
1               5                   10

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggagccgtac atgaactgag ggg                                              23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aagtaaaacc tctacaaatg                                                  20
```

NANOCAPSULE DELIVERY SYSTEM FOR RIBONUCLEOPROTEINS

CROSS-REFERENCE TO RELATED APPLICATIONS

This application claims the benefit of and priority to U.S. Provisional Patent Application No. 62/551,202, filed Aug. 28, 2017, the entire contents of which are incorporated herein by reference.

GOVERNMENT RIGHTS

This invention was made with government support under GM119644 and awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Oct. 24, 2018, is named 032026-1379_SL.txt and is 14,508 bytes in size.

FIELD

The present technology relates generally to the field of encapsulated ribonucleoprotein delivery systems. The compositions of such systems include a polymeric shell encapsulating a Cas9 polypeptide complexed with a guide RNA.

BACKGROUND

Gene editing is anticipated to modify mutations responsible for human disease and introduce new genetic functionality into the human body. For somatic gene editing applications both in vivo and ex vivo, delivery of the CRISPR nuclease along with its single-guide RNA (sgRNA) into cells is a significant challenge. Viral delivery of CRISPR components is commonly used for delivery of the nuclease and sgRNA into cells, but viral vectors raise additional safety concerns for clinical application. While nonviral delivery of plasmids and mRNA can be used, they rely on transcription and/or translational machinery of the host cells. Plasmids also carry the risk of insertional mutagenesis into the host genome. In contrast, delivering a pre-assembled CRISPR nuclease protein (e.g., Sp. Cas9, a commonly-used example) with the sgRNA, together called a ribonucleoprotein (RNP), does not rely on such cellular machinery for precise enzymatic gene editing activity nor carry any long nucleic acids that could integrate into the genome. Importantly, RNP delivery strategies exhibit lower off-target mutagenesis, due the shorter life time of CRISPR complex within the cell before degradation compared to plasmid or mRNA delivery strategies. These characteristics make RNP delivery attractive for clinical use. To date, however, delivering RNPs using nonviral biomaterials specifically to a cell type of interest within the body or ex vivo in culture occurs with only limited success.

SUMMARY OF THE INVENTION

The present technology provides nanoencapsulated ribonucleoprotein (RNP) complexes with improved delivery of the RNP inside targeted cells while maintaining high levels of activity by the RNP. Thus in one aspect, the present technology provides a nanocapsule (aka, NC) including an RNP as a core and a biodegradable crosslinked polymer shell (referred to herein as "the polymer shell") that encapsulates the core. The RNP complex includes a Cas9 polypeptide and a guide RNA. The polymer shell is made of polymerized monomers of imidazolyl acryloyl monomers, bisacryloyl disulfides (a biodegradable cross-linker), optionally poly(ethylene glycol) (PEG) acryloyl monomers, and either cationic acryloyl monomers, anionic acryloyl monomers, or both cationic and anionic acryloyl monomers (optionally in combination with non-ionic monomers). A schematic of an illustrative embodiment of formation of the nanocapsule using various acryloyl monomers is shown in FIG. 1A. When present, the PEG chains extending from the nanocapsule are believed to help solubilize the nanocapsule and provide a convenient attachment point for cell targeting ligands, cell penetrating peptides (CPP), imaging agents and the like. It will be understood by those of skill in the art that the nanocapsules of the present technology exist as salts due to the inclusion of ionizable groups including, e.g., but not limited to carboxylic acids, amines, and phosphates.

While not wishing to be bound by theory, it is believed that the polymer shell protects the RNP from degradation in the extracellular environment and assists in delivery of the RNP into cells as shown in the schematic of FIG. 1B. The small size of the nanocapsules (e.g., having a hydrodynamic diameter of about 7 to about 25 nm) as well as any CPP and/or targeting ligand present allow the nanocapsules to enter the target cells by endocytosis. The presence of the imidazolyl groups in the polymer shell facilitate endosomal escape of the nanocapsules, because imidazole groups, having a pKa value of ~6.0, can take up protons in the acidic endosomes. This absorption of protons leads to endosomal-membrane disruption as previously described (G. Chen, Y. Wang, R. Xie, S. Gong, $J.$ $Control.$ $Release$ 2017, 259, 10), thereby enabling release of the nanocapsules into the cytosol. There, due to the glutathione (GSH)-rich environment of the cytosol (2-10 mM), the disulfide bonds of the biodegradable cross-linkers are reduced, causing the polymer shell to degrade. Once released from the nanocapsules, RNPs can enter the nucleus, optionally facilitated by one or more nuclear localization signals (NLSs), on Cas9 proteins, and perform its gene editing functions.

BRIEF DESCRIPTION OF THE DRAWINGS

FIG. 1A shows a schematic illustration for the formation of the covalently-crosslinked, yet intracellularly biodegradable NC for the delivery of the RNP complex prepared by in situ free radical polymerization. FIG. 1B shows a schematic depiction of proposed mechanism of cellular uptake of RNP NCs and the subcellular release.

FIGS. 4A-D graphically show an illustrative embodiment of the uptake of Atto-550 tagged gRNA in RNP nanocapsules in HEK 293 cells. FIG. 4A shows results of the MTT assay of cell viability after treatment with various combinations of Cas9 RNP, Lipo 2000 and NCs.

FIGS. 4B and 4C show (respectively) representative histograms and quantification of mCherry gene editing measured through flow cytometry of untransfected HEK293s or cells transfected with RNP using Lipo 2000 or NCs. SgRNAs within the RNPs targeted the mCherry transgene, and thus gene editing can be assayed by the loss of mCherry fluorescence within cells. NCs of FIGS. 4A-4C were prepared using Method I in the Examples with an a/b/c/d/e ratio of monomers of 337/225/38/70/10. NCs of FIG. 4D were prepared using Method II in the Examples with an a/b/c/d/e ratio of monomers of 927/927/244/231/33.

FIGS. 5A-5B show (respectively) representative histograms and quantification of mCherry gene editing measured using flow cytometry of untransfected H9 stem cells or cells transfected with RNP using Lipo 2000 or NC-3. sgRNAs within the RNPs targeted the mCherry transgene, and thus gene editing can be assayed by the loss of mCherry fluorescence within cells. NCs were prepared using Method I in the Examples with an a/b/c/d/e ratio of monomers of 337/225/38/70/10.

FIGS. 6A-6B show (respectively) representative histograms and quantification of mCherry gene editing measured using flow cytometry of untransfected Jurkats or cells transfected with RNP using Lipo 2000 or NC-3. sgRNAs within the RNPs targeted the mCherry transgene, and thus gene editing can be assayed by the loss of mCherry fluorescence within cells. NCs were prepared using Method I in the Examples with an a/b/c/d/e ratio of monomers of 337/225/38/70/10.

DETAILED DESCRIPTION

Figure 1A:
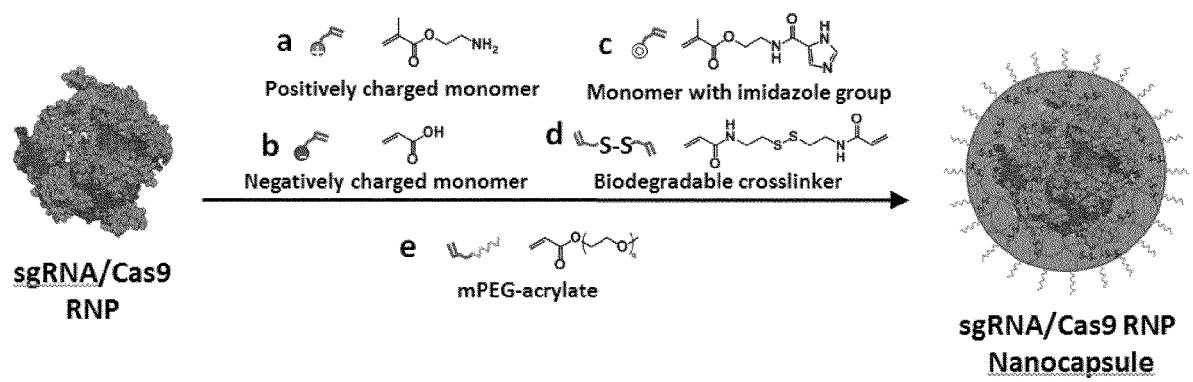
FIGS. 1A, 1B are schematics of illustrative embodiments of the present technology.
Figure 1B:
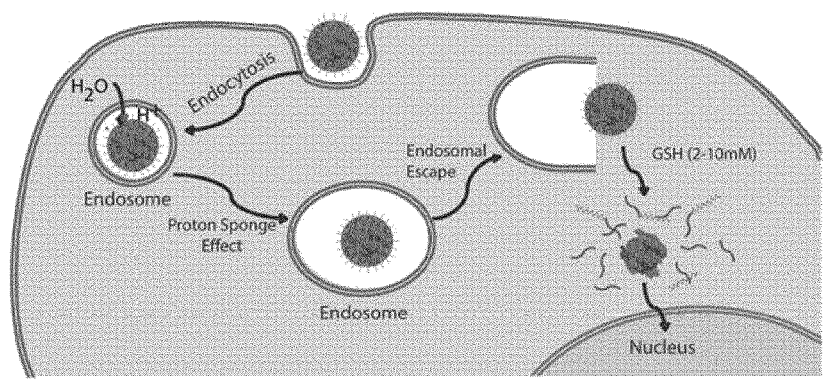

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, Cas9 polypeptide refers to Cas9 proteins and variants thereof having nuclease activity, as well as fusion proteins containing such Cas9 proteins and variants thereof. The fused proteins may include those that modify the epigenome or control transcriptional activity. The variants may include deletions or additions, such as, e.g., addition of one, two, or more nuclear localization sequences (such as from SV40 and others known in the art), e.g., 1, 2, 3, 4, 5, 6, 7, 8, 9, 10 such sequences or a range between and including any two of the foregoing values. In some embodiments the Cas9 polypeptide is a Cas9 protein found in a type II CRISPR-associated system. Suitable Cas9 polypeptides that may be used in the present technology include, but are not limited to Cas9 protein from *Streptococcus pyogenes* (Sp. Cas9), *F. novicida, S. aureus, S. thermophiles, N. meningitidis*, and variants thereof. In some embodiments, the Cas9 polypeptide is a wild-type Cas9, a nickase, or comprises a nuclease inactivated (dCas9) protein. In some embodiments, the Cas9 polypeptide is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., TET1, p300). In some embodiments, the Cas9 polypeptide includes variants with at least 85% sequence identity, at least 90% sequence identity, at least 95% sequence identity, or even 96%, 97%, 98%, or 99% sequence identity to the wild type Cas9. Accordingly, a wide variety of Cas9 polypeptides may be used in the present nanocapsules as encapsulation is not sequence dependent so long as the surface of the Cas9 polypeptide has sufficient positive and/or negatively charged residues to allow coating by the anionic and/or cationic acryloyl-based monomers of the present technology. Other suitable Cas9 polypeptides may be found in Karvelis, G. et al. "Harnessing the natural diversity and in vitro evolution of Cas9 to expand the genome editing toolbox," *Current Opinion in Microbiology* 37: 88-94 (2017); Komor, A. C. et al. "CRISPR-Based Technologies for the Manipulation of Eukaryotic Genomes," *Cell* 168:20-36 (2017); and Murovec, J. et al. "New variants of CRISPR RNA-guided genome editing enzymes," *Plant Biotechnol. J.* 15:917-26 (2017), each of which is incorporated by reference herein.

"Molecular weight" as used herein with respect to polymers refers to weight average molecular weights (Mw) and can be determined by techniques well known in the art including gel permeation chromatography (GPC). GPC analysis can be performed, for example, on a D6000M column calibrated with poly(methyl methacrylate) (PMMA) using triple detectors including a refractive index (RI) detector, a viscometer detector, and a light scattering detector, and dimethylformamide as the eluent. "Molecular weight" in reference to small molecules and not polymers is actual molecular weight, not an average weight.

The phrase "targeting ligand" refers to a ligand that binds to "a targeted receptor" that distinguishes the cell being targeted for gene editing. The ligands may be capable of binding due to expression or preferential expression of a receptor for the ligand, accessible for ligand binding, on the target cells. Examples of such ligands include GE11 peptide, anti-EGFR nanobody, cRGD ((cyclo(RGDfC)), KE108 peptide, octreotide, folic acid, prostate-specific membrane antigen (PSMA) aptamer, TRC105, a human/murine chimeric IgG1 monoclonal antibody, mannose, and cholera toxin B (CTB). Additional examples of such ligands include Rituximab, Trastuzumab, Bevacizumab, Alemtuzumab, Panitumumab, RGD, DARPins, RNA aptamers, DNA aptamers, analogs of folic acid and other folate receptor-binding molecules, lectins, other vitamins, peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selecting, steroid hormones, Arg-Gly-Asp containing peptides, microtubule-associated sequence (MTAS), various galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of targeted cells or on an infectious organism, or fragments of any of these molecules.

The phrase "a targeted receptor" refers to a receptor expressed by a cell that is capable of binding a cell targeting ligand. The receptor may be expressed on the surface of the cell. The receptor may be a transmembrane receptor. Examples of such targeted receptors include EGFR, $α_vβ_3$ integrin, somatostatin receptor, folate receptor, prostate-specific membrane antigen, CD105, mannose receptor, estrogen receptor, and GM1 ganglioside.

In some embodiments, a cell penetrating peptide may also be attached to one or more PEG terminal groups in place of or in addition to the targeting ligand. A "cell penetrating peptide" (CPP), also referred to as a "protein transduction domain" (PTD), a "membrane translocating sequence," and a "Trojan peptide", refers to a short peptide (e.g., from 4 to about 40 amino acids) that has the ability to translocate across a cellular membrane to gain access to the interior of a cell and to carry into the cells a variety of covalently and noncovalently conjugated cargoes, including proteins, oligonucleotides, and liposomes. They are typically highly cationic and rich in arginine and lysine amino acids. Examples of such peptides include TAT cell penetrating peptide (GRKKRRQRRRPQ (SEQ ID NO: 4)); MAP (KLAL) KLALKLALKALKAALKLA (SEQ ID NO: 5); Penetratin or Antenapedia PTD RQIKWFQNRRMKWKK (SEQ ID NO: 6); Penetratin-Arg: RQIRIWFQNRRMRWRR (SEQ ID NO: 7); antitrypsin (358-374): CSIPPEVKFNKPFVYLI (SEQ ID NO: 8); Temporin L: FVQWFSKFLGRIL-NH2(SEQ ID NO: 9); Maurocalcine: GDC(acm)LPHLKLC (SEQ ID NO: 10); pVEC (Cadherin-5): LLIILRRRIRKQAHAHSK (SEQ ID NO: 11); Calcitonin: LGTYTQDFNKFHTFPQTAIGVGAP (SEQ ID NO: 12); Neurturin: GAAEAAARVYDLGLRRLRQRRRLRRERVRA (SEQ ID NO: 13); Penetratin: RQIKIWFQNRRMKWKKGG (SEQ ID NO: 14); TAT-HA2 Fusion Peptide: RRRQRRKKRGGDIMGEWGNEIFGAIAGFLG (SEQ ID NO: 15); TAT (47-57) YGRKKRRQRRR (SEQ ID NO: 16); SynB1 RGGRLSYSRRRFSTSTGR (SEQ ID NO: 17); SynB3 RRLSYSRRRF (SEQ ID NO: 18); PTD-4 PIRRRKKLRRL (SEQ ID NO: 19); PTD-5 RRQRRTSKLMKR (SEQ ID NO: 20); FHV Coat-(35-49) RRRRNRTRRNRRRVR (SEQ ID NO: 21); BMV Gag-(7-25) KMTRAQRRAAARRNRWTAR (SEQ ID NO: 22); HTLV-II Rex-(4-16) TRRQRTRRARRNR (SEQ ID NO: 23); HIV-1 Tat (48-60) or D-Tat GRKKRRQRRRPPQ (SEQ ID NO: 24); R9-Tat GRRRRRRRRRPPQ (SEQ ID NO: 25); Transportan GWTLNSAGYLLGKINLKALAALAKKIL chimera (SEQ ID NO: 26); MAP KLALKLALKLALALKLA (SEQ ID NO: 27); SBP or Human P1 MGLGLHLL-VLAAALQGAWSQPKKKRKV (SEQ ID NO: 28); FBP GALFLGWLGAAGSTMGAWSQPKKKRKV (SEQ ID NO: 29); MPG ac-GALFLGFL-GAAGSTMGAWSQPKKKRKV-cya (SEQ ID NO: 30) (wherein cya is cysteamine); MPG(ΔNLS) ac-GALFLGFL-GAAGSTMGAWSQPKSKRKV-cya (SEQ ID NO: 31); Pep-1 or Pep-1-Cysteamine ac-KETWWETWWTEWS-QPKKKRKV-cya (SEQ ID NO: 32); Pep-2 ac-KETWFETWFTEWSQPKKKRKV-cya (SEQ ID NO: 33); Periodic sequences, Polyarginines R×N (4<N<17) (SEQ ID NO: 34) chimera; Polylysines K×N (4<N<17) (SEQ ID NO: 35) chimera; (RAca)6R(SEQ ID NO: 36); (RAbu)6R(SEQ ID NO: 37); (RG)6R(SEQ ID NO: 38); (RM)6R(SEQ ID NO: 39); (RT)6R(SEQ ID NO: 40); (RS)6R(SEQ ID NO: 41); R10(SEQ ID NO: 42); (RA)6R (SEQ ID NO: 43); and R7(SEQ ID NO: 44).

A "dye" refers to small organic molecules having a molecular weight (actual, not weight average) of 2,000 Da or less or a protein which is able to emit light. Non-limiting examples of dyes include fluorophores, chemiluminescent or phosphorescent entities. For example, dyes useful in the present technology include but are not limited to cyanine dyes (e.g., Cy2, Cy3, Cy5, Cy5.5, Cy7, and sulfonated versions thereof), fluorescein isothiocyanate (FITC), ALEXA FLUOR® dyes (e.g., ALEXA FLUOR® 488, 546, or 633), DYLIGHT® dyes (e.g., DYLIGHT® 350, 405, 488, 550, 594, 633, 650, 680, 755, or 800) or fluorescent proteins such as GFP (Green Fluorescent Protein).

In one aspect the present technology provides a nanocapsule having a single ribonucleoprotein (RNP) complex as a core and a biodegradable crosslinked polymer shell that encapsulates the core, wherein the RNP complex includes a Cas9 polypeptide and a guide RNA, and the polymer shell includes polymerized monomers of imidazolyl acryloyl monomers, PEG acryloyl monomers, bisacryloyl disulfide monomers, and either cationic acryloyl monomers, anionic acryloyl monomers, or both cationic and anionic acryloyl monomers. Targeting ligands and/or cell penetrating peptides (CPP) may also be attached to the polymer shell, e.g., via the PEG acryloyl monomers.

Guide RNAs direct Cas-9 polypeptides to cut DNA at specific genomic locations. Any suitable guide RNA may be used in the RNP of the present nanocapsules. In some embodiments, the guide RNA is a modified guide RNA such as, e.g., a single guide RNA (sgRNA). In some embodiments, the modified guide RNA includes a crRNA comprising, from a single-stranded protospacer sequence, a protospacer adjacent motif for a Cas9 polypeptide, and a first complementary strand of a binding region for the Cas9 polypeptide, and a tracrRNA comprising, a second complementary strand of the binding region for the Cas9 polypeptide, wherein the crRNA or the tracrRNA optionally comprises an aptamer that binds a biotin-binding molecule, and wherein the crRNA and the tracrRNA hybridize through the first and second complementary strands of the binding region for the Cas9 polypeptide. In some such embodiments, the crRNA and the tracrRNA form an sgRNA, the sgRNA comprising, from 5' to 3', the single-stranded protospacer sequence, the protospacer adjacent motif for a Cas9 polypeptide, the first complementary strand of a binding region for the Cas9 polypeptide, the optional aptamer that binds a biotin-binding molecule, and the second complementary strand of the binding region for the Cas9 polypeptide. In still other embodiments, in the secondary structure of the modified sgRNA, the binding region for the Cas9 polypeptide and the aptamer that binds the biotin-binding molecule (when present) form a stem-loop structure. In some embodiments, the sgRNA is chemically modified as shown in AA. Hendel et al. *Nature Biotech.* (2015), 33:985-89, incorporated herein by reference in its entirety. Other suitable sgRNA may be found in U.S. Provisional Patent Application No. 62/519, 317, ("Modified Guide RNAs, CRISPR-Ribonucleoprotein Complexes and Methods of Use"), incorporated herein by reference in its entirety.

In some embodiments of the present nanocapsules, the modified guide RNA has the sequence

```
                                              (SEQ ID NO: 1)
NNNNNNNNNNNNNNNNNNNNNGUUUAAGAGCUAUGCUGCGAAUACGAGAUG

CGGCCGCCGACCAGAAUCAUGCAAGUGCGUAAGAUAGUCGCGGGUCGGCG

GCUCGUAUUCGCAGCAUAGCAAGUUUAAAUAAGGCUAGUCCGUUAUCAAC

UUGAAAAAGUGGCACCGAGUCGGUGCUUUU;

(SEQ ID NO: 2)
NNNNNNNNNNNNNNNNNNNNNGUUUAAGAGCUAUGCUGGAAACAGCAUAGC

AAGUUUAAAUAAGGCUAGUCCGUUAUCAACUUCGAAUACGAGAUGCGGCC

GCCGACCAGAAUCAUGCAAGUGCGUAAGAUAGUCGCGGGUCGGCGGCUCG

UAUUCGGAAAAAGUGGCACCGAGUCGGUGCUUUU;
or
                                              (SEQ ID NO: 3)
NNNNNNNNNNNNNNNNNNNNNGUUUAAGAGCUAUGCUGGAAACAGCAUAGC

AAGUUUAAAUAAGGCUAGUCCGUUAUCAACUUGAAAAAGUGGCACCGAGU

CGGUGCCGAAUACGAGAUGCGGCCGCCGACCAGAAUCAUGCAAGUGCGUA

AGAUAGUCGCGGGUCGGCGGCUCGUAUUCGUUUU.
```

In some embodiments, the gene to be edited is a gene that is a therapeutic target, for example a gene that is desirable to inactivate or correct in the treatment of a disease. In some embodiments, the targeted nucleic acid sequence is a CEP90, CCR5, DMD, NRL, B2M, HBB, PD1, TRAC, BEST1, MERTK, PRDM16, PPARγ, VEGF-A, Oct-4, PI3K, presenilin, α-antitrypsin, von willebrand factor, or caspase-9 gene sequence.

The nanocapsules of the present technology include a thin biodegradable crosslinked polymer shell encapsulating the RNP. The polymer shell is prepared using a mass of acryloyl-based monomers of the types described herein which is similar to the mass of the RNP. For example, the mass ratio between the polymer shell and the RNP may range from 0.4 to 10.0, although lower and higher ratios may also be suitable depending on the RNP used. In some cases, the mass ratio ranges from 0.4 to 3.5, and in others from 0.4 to 1.2 or even 0.6 or 0.7 to 3.5, 2.0 or 1.2. Suitable mass ratios may thus include 0.4, 0.5, 0.6, 0.7, 0.8, 0.9, 1.0, 1.1, 1.2, 1.3, 1.4, 1.5, 1.6, 1.7, 1.8, 2.0, 2.2, 2.5, 3.0, 3.5, 4.0, 4.5, 5.0, 5.5, 6.0, 6.5, 7.0, 8.0, 9.0, 10.0 or any range of values between and including any two of the foregoing values.

While the polymer shell may include polymerized cationic acryloyl monomers or polymerized anionic acryloyl monomers, it may also include both polymerized cationic and anionic acryloyl monomers. Optionally, the polymer shell may include polymerized non-ionic acryloyl monomers. Thus, in some embodiments, the polymer shell includes polymerized monomers of both cationic and non-ionic acryloyl monomers, polymerized monomers of both anionic and non-ionic acryloyl monomers, or polymerized monomers of cationic, anionic and non-ionic monomers. In some embodiments, the mole ratio of polymerized cationic acryloyl monomers to polymerized anionic acryloyl monomers and/or to polymerized non-ionic monomers may range from 10:1 to 1:10. Similarly, the ratio of polymerized anionic to non-ionic monomers may range from 10:1 to 1:10. Suitable mole ratios of such polymerized monomers include 10:1, 9:1, 8:1, 7:1, 6:1, 5:1, 4:1, 3:1, 2:1, 3:2, 1:1, 2:3, 1:2, 1:3, 1:4, 1:5, 1:6, 1:7, 1:8, 1:9, 1:10, or a range of values between and including any two of the foregoing, such as, e.g., 3:1 to 1:3. The mole ratio of all polymerized monomers (e.g., anionic acryloyl, and/or cationic acryloyl, and/or non-ionic acryloyl, and optional PEG acryloyl monomers, and imidazolyl acryloyl monomers and bisacryloyl disulfide monomers) to RNP may range from 400:1 to 8000:1, although higher ratios may also be used. Suitable mole ratios of all charged acryloyl monomers to RNP include 400:1, 500:1, 600:1, 700:1, 800:1, 900:1, 1000:1, 1100:1, 1200:1, 1300:1, 1400:1, 1500:1, 1600:1, 1800:1, 2000:1, 2200:1, 2500:1, 3000:1, 3500:1, 4000:1, 4500:1, 5000:1, 6000:1, 6500:1, 7000:1, 7500:1, or 8000:1 or a range between and including any two of the foregoing values.

Acryloyl monomers of the present technology include acrylic acid and methacrylic acid monomers (and salts thereof), esters of such monomers and amides of such monomers. The esters and amides may bear positively charged groups such as amines, amidines or guanidines, or negatively charged groups such as carboxyls, sulfonates, and phosphates. For example, the cationic acryloyl monomer of the present technology may have the structure of Formula (I):

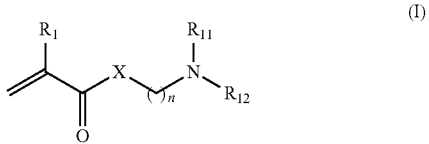

wherein
$R_1$ is H or methyl;
$R_{11}$ is H or methyl or ethyl;
$R_{12}$ is H or methyl or ethyl;
X is O or NH; and
n is 0, 1, 2, 3, 4, 5, or 6.
In some embodiments of the monomer of Formula (I), $R_{11}$ and $R_{12}$ are each H. In some embodiments, the cationic acryloyl monomer has the structure of Formula (IA):

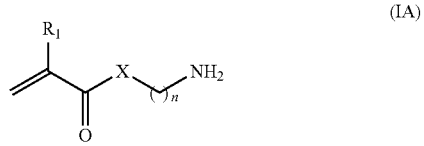

wherein
$R_1$ is H or methyl;
X is O or NH; and
n is 0, 1, 2, 3, 4, 5, or 6.
In some embodiments of the monomers of Formula (I) or (IA), $R_1$ is H. In certain embodiments, $R_1$ is methyl. In some embodiments, X is NH. In some embodiments, n is 1, 2, 3, 4, 5, or 6. In some embodiments, n is 2 or 3. In some embodiments, when n is 0, X is NH.

Similarly, the anionic acryloyl monomer of the present technology may have the structure of Formula II:

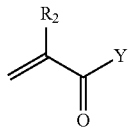

(II)

wherein $R_2$ is H or methyl;

Y is OH, —O—$(CH_2)_m$—COOH, —O—$(CH_2)_m$—$SO_3H$, —O—$(CH_2)_m$—$OPO_3H_2$, —NH—$(CH_2)_m$—COOH, —NH—$(CH_2)_m$—$SO_3H$, or —NH—$(CH_2)_m$—$OPO_3H_2$; and m is 1, 2, 3, 4, 5, or 6.

The polymer shell optionally includes polymerized monomers of non-ionic acryloyl monomers. Such monomers remain uncharged in aqueous solution, but do not include acryloyl monomers having non-ionic polymers attached such as PEG acryloyl monomers. In some embodiments, the non-ionic acryloyl monomers have the structure of Formula III:

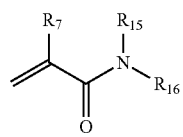

(III)

wherein $R_7$ is H or methyl;

$R_{15}$ and $R_{16}$ are each independently H, methyl, ethyl, propyl, or isopropyl.

In some embodiments, $R_7$ is H. In certain embodiments, $R_{15}$ and $R_{16}$ are both H.

Imidazolyl acryloyl monomers of the present technology include esters and amides of acrylic/methacrylic acid that contain an imidazole group. For example, the imidazolyl acryloyl monomer may have the structure of Formula IV:

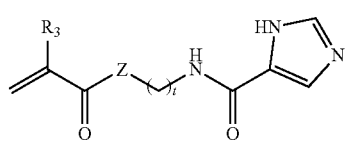

(IV)

wherein $R_3$ is H or methyl;

Z is O or NH; and t is 1, 2, 3, 4, 5, or 6.

In other embodiments, the imidazolyl acryloyl monomer has the structure of Formula IV-2:

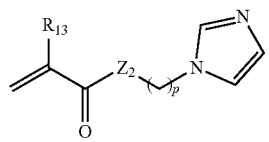

(IV-2)

wherein $R_{13}$ is H or methyl;

$Z_2$ is O or NH; and p is 1, 2, 3, 4, 5, or 6.

In other embodiments, the imidazolyl acryloyl monomer has the structure of Formula IV-3:

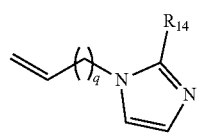

(IV-3)

wherein $R_{14}$ is H or methyl;

q is 0, 1, 2, 3, 4, 5, or 6.

In some embodiments of the imidazolyl acryloyl monomers of Formulae (IV), (IV-2) and (IV-3), $R_3$ or $R_{13}$ or $R_{14}$ is H. In certain embodiments, Z or $Z_2$ is NH. In some embodiments, t is 2 or 3 or p is 2 or 3. In some embodiments, q is 1, 2, or 3.

Less imidazolyl acryloyl monomer is used to prepare the polymer shell than the anionic/cationic acryloyl monomers. For example the mole ratio of imidazolyl acryloyl monomer to RNP may be 20:1 to 800:1. Suitable mole ratios include 20:1, 30:1, 40:1, 50:1, 60:1, 70:1, 80:1, 90:1, 100:1, 110:1, 120:1, 150:1, 200:1, 250:1, 300:1, 400:1, 500:1, 600:1, 700:1, 800:1 or a range between and including any two of the foregoing values, e.g., 20:1 to 400:1 or 20:1 to 60:1.

As noted above, the polymer shell includes bisacryloyl disulfide monomers designed to crosslink the polymer shell, but to degrade once the nanocapsule is released into the cytosol of the target cell. For example the bisacryloyl disulfide may have the structure of Formula V:

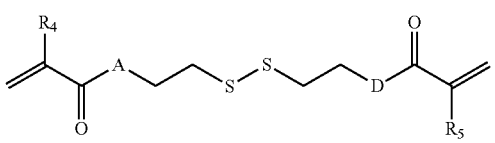

(V)

wherein

A and D are independently selected from 0 and NH; and $R_4$ and $R_5$ are independently selected from H and methyl.

In some embodiments of bisacryloyl disulfide of Formula V, A and D are each NH. In certain embodiments of Formula V, $R_4$ and $R_5$ are each H. In some embodiments, the mole ratio of bisacryloyl disulfide to RNP may be 50:1 to 1000:1. Suitable mole ratios include 50:1, 60:1, 70:1, 80:1, 90:1, 100:1, 110:1, 120:1, 130:1, 140:1, 150:1, 160:1, 170:1, 180:1, 190:1, 200:1, 210:1, 250:1, 300:1, 350:1, 400:1, 500:1, 600:1, 700:1, 800:1, 900:1, 1000:1 or a range between and including any two of the foregoing values.

In some embodiments of the present NCs, the polymerized shell includes polymerized PEG acryloyl monomers. The PEG acryloyl monomer can be an ester or amide of an acrylic/methacrylic acid containing PEG. In some embodiments, PEG acryloyl monomer has the structure of Formula VI:

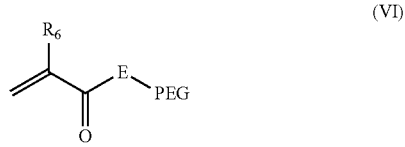

wherein

E is O or NH; and $R_6$ is H or methyl; and

PEG is polyethylene glycol having a weight average molecular weight of 100 Da to 10000 Da. In some embodiments the PEG has a weight average molecular weight of 100, 250, 500, 1000, 1500, 2000, 2500, 3000, 4000, 5000 or 10000 Da or a range between and including any two of the foregoing values. For example, the PEG molecular weight may be 500 to 5000.

Each PEG terminates in one of various groups selected from a targeting ligand, OH, O—($C_{1-6}$)alkyl, $NH_2$, biotin, a cell penetrating peptide, a dye or other imaging agent. For example, the imaging agent may be a chelating agent for isotopes (e.g., triazacyclononane-phosphinic acid (i.e., TRAP), 1,4,7,10-tetraazacyclododecane-1,4,7,10-tetraacetic acid (i.e., DOTA), 1,4,7-triazacyclononane-triacetic acid (i.e., NOTA), diethylenetriaminepentaacetic acid (i.e., DTPA), or chelating peptides). Thus, the imaging agent may be one for PET or MRI. In some embodiments the PEG terminates in OH or O—($C_{1-6}$)alkyl, and in still others the PEG terminates in an $OC_{1-3}$ alkyl group. In some embodiments, the PEG terminates in a targeting ligand. The targeting ligand may be selected from the group consisting of a cofactor, carbohydrate, peptide, antibody, nanobody, or aptamer. In other embodiments, the targeting ligand or CPP is selected from the group consisting of folic acid, mannose, GE11, anti-EGFR nanobody, cRGD, KE108, octreotide, TAT cell penetrating peptide, PSMA aptamer, TRC105, and CTB. The targeting ligand may be attached to the PEG via a reactive linker such as maleimide or N-hydroxysuccinimide. The mole ratio of PEG acryloyl monomer to RNP may range from 0:1 or 1:1 to 30:1, e.g., 0:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, or a range between and including any two of the foregoing values.

In another aspect, there are provided methods of making nanocapsules of the present technology. The RNP may be made by combining Cas9 and the desired guide RNA in a buffered aqueous solution as described herein or in accordance with known methods. Because the RNP exhibits heterogeneous surface charges on the protein and sgRNA, cationic and/or anionic acryloyl monomers form a coating around the RNP through electrostatic interaction. The imidazolyl acryloyl monomer, bisacryloyl disulfide, and PEG acryloyl (when present) are also attracted to the surface of the RNP complex via van der Waals interactions. The nanocapsules described herein thus may be made simply by mixing the RNP in a buffered aqueous solution with the cationic and/or anionic acryloyl monomers, followed by with the imidazolyl acryloyl and biodegradable cross-linker in the mole ratios of monomers to RNP as described herein. A first polymerization (e.g., ammonium persulfate/TMEDA initiated) is carried out for a time (e.g., 30-90 min), after which the PEG acryloyl(s) (when present) are added to the mixture and a second polymerization is carried out to incorporate the PEG groups into the polymer shell.

In another aspect, the present technology provides a kit including any of the nanocapsules described herein, as well as compositions comprising any of the nanocapsule disclosed herein and a pharmaceutically acceptable carrier. The compositions may be used in the methods described herein. In one aspect the present technology provides a method for delivering an RNP to a cell to modify a target gene comprising exposing the cell to an effective amount of a nanocapsule. The cell may be in vitro or in vivo. "Effective amount" refers to the amount of nanocapsule required to produce a desired effect. One example of an effective amount includes amounts or dosages that produce the desired gene editing in the target cells. Where the cell is in vivo, the effective amount is delivered to a subject, e.g., a subject in need thereof. As used herein, a "subject" is a mammal, such as a cat, dog, rodent or primate. In some embodiments, the subject is a human.

The compositions described herein can be formulated for various routes of administration, for example, by parenteral, intravitreal, intrathecal, intracerebroventricular, rectal, nasal, vaginal administration, direct injection into the target organ, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the nanoparticles described herein. Injectable forms may be prepared with acceptable solvents or vehicles including, but not limited to sterilized water, phosphate buffer solution, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. Exemplary carriers and excipients may include but are not limited to USP sterile water, saline, buffers (e.g., phosphate, bicarbonate, etc.), tonicity agents (e.g., glycerol), Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the present nanocapsules to the patient and may include 0.1, 0.2, 0.3, 0.4, 0.5, 0.75, 1.0, 1.5, 2.0, 2.5, 3.0, 4.0, 5.0, 6.0, 7.0, 8.0, 9.0, 10, 11, 12, 13, 14, 15 mg/kg or a range between and including any two of the forgoing values such as 0.1 to 15 mg/kg. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

In another aspect, the present technology provides kits including the components needed to prepare any of the compositions described herein. For example, a kit may include a package containing a nanocapsule as described herein and directions for use of the kit. In another embodiment, the kit includes a Cas9 polypeptide and the acrylic monomers and other reagents needed for preparing a nanocapsule of the present technology as well as directions for preparing the nanocapsule. The user would provide the desired gRNA or it could be supplied with the kit. The present kits allow the user to prepare the delivery composition described herein by first preparing the RNP and then encapsulating it in accord with the present technology, and/or to employ the nanocapsules in editing the genetic loci within the target cells.

The examples herein are provided to illustrate advantages of the present technology and to further assist a person of ordinary skill in the art with preparing or using the nanoparticle compositions of the present technology. To the extent that the compositions include ionizable components, salts such as pharmaceutically acceptable salts of such components may also be used. The examples herein are also presented in order to more fully illustrate the preferred aspects of the present technology. The examples should in no way be construed as limiting the scope of the present technology, as defined by the appended claims. The examples can include or incorporate any of the variations or aspects of the present technology described above. The variations or aspects described above may also further each include or incorporate the variations of any or all other variations or aspects of the present technology.

EXAMPLES

General

Materials. N,N'-bis(acryloyl)cystamine (BACA), 1-vinylimidazole (VI), N,N,N',N'-tetramethylethylenediamine (TMEDA), N,N'-methylenediacrylamide (BAA), tris (2-carboxyethyl) phosphine (TCEP), and ammonium persulfate (APS) were purchased from Thermo Fisher Scientific (Fitchburg, Wis., USA). Acrylic acid (AA), acrylated PEG (APEG; 480 Da), and N-(3-aminopropyl) methacrylamide hydrochloride (APMA) were purchased from Sigma-Aldrich (St. Louis, Mo., USA). Acrylated PEG-Maleimide (APEG-Mal; 2 KDa) and acylated PEG-N-hydroxysuccinimide (APEG-NHS; 2 KDa) were purchased from Creative PEGWorks (Chapel Hill, N.C., USA). Cell penetrating peptide (CPP) and TAT-Cys (CYGRKKRRQRRR (SEQ ID NO: 45)) were synthesized by Genscript (Piscataway, N.J., USA).

Cell Culture. Human embryonic kidney (HEK), normal human dermal fibroblast (NHDF) and M21 melanoma cell lines were maintained on Gelatin-A coated plates at passage 10-50 in Dulbecco's modified Eagle medium (DMEM) supplemented with 10% fetal bovine serum (FBS), 2 mM L-Glutamine and 50 U/mL Penicillin/Streptomycin. Jurkats were maintained in suspended culture in RPMI 1640 with 10% FBS and 50 U/mL Penicillin/Streptomycin. WA09 WA09 human embryonic stem cells (hESCs) (WiCell, Madison, Wis.) were maintained in mTESR medium on Matrigel (WiCell) coated tissue culture polystyrene plate (BD Falcon). hESCs were passaged every 3-4 days at a 1:6 ratio using Versene solution (Life Technologies).

H2B-mCherry transgenic lines were generated as previously reported (T. Harkness, J. D. Mcnulty, R. Prestil, S. K. Seymour, T. Klann, M. Murrell, R. S. Ashton, K. Saha, *Biotechnol. J.* 2015, 10, 1555; Steyer, B., Carlson-Stevermer, J., Angenent-Mari, N., Khalil, A., Harkness, T., and Saha, K. (2016) *Acta Biomater* 34, 143-158) through CRISPR-mediated insertion of a modified AAV-CAGGS-EGFP plasmid (Addgene #22212) at the AAVS1 safe harbor locus using gRNA AAVS1-T2 (Addgene #41818). All cells were maintained at 37° C. and 5% $CO_2$. Cell lines were kept mCherry positive through puromycin selection or fluorescence assisted cell sorting (FACS) on a BD FACS Aria.

Example 1: Preparation of RNP sgRNAs In Vitro Transcription. A DNA double stranded template of a truncated T7 promoter and desired sgRNA sequence was formed through overlap PCR using Q5 high fidelity polymerase (New England Biolabs) according to manufacturer's protocols and was placed in the thermocycler for 35 cycles of 98° C. for 5 s, 52° C. for 10 s, and 72° C. for 15 s, with a final extension period of 72° C. for 10 min. PCR products were then incubated overnight at 37° C. in a HiScribe T7 in vitro transcription reaction (New England Biolabs) according to manufacturer's protocol. The resulting RNA was purified using a MEGAclear Transcription Clean-Up Kit (Thermo Fisher). sgRNA concentration was quantified using a Qubit fluorometer (Thermo Fisher). The sgRNA sequence targeting mCherry (with PAM site) is as follows: GGAGCCGTACATGAACTGAG GGG (SEQ ID NO: 46).

Preparation of Nanocapsules (NCs), Method I. sNLS-Cas9-sNLS protein (Aldevron, Madison, Wis.) was combined with the desired sgRNA at a 1:1 ratio and allowed to complex for 5 minutes with gentle mixing. Cas9 RNP complex was diluted to 250 ng/mL in 5 mM sodium bicarbonate buffer (pH=8.5). Monomers were added into the above solution under stirring in the order of AA, AEMA, and 2-(1H-imidazol-2-carboxamido)ethyl methacrylate (ICEMA) at 5 min intervals. After another 5 min, the crosslinker, BACA, was added, followed by the addition of ammonium persulfate (2 µL; 10 mg/mL in sodium bicarbonate buffer). The mixture was degassed for 10 min, and the polymerization reaction was immediately initiated by the addition of TMEDA (3 µL; 10 mg/mL in degassed DI water). After 50 min of polymerization, the APEG was added. The reaction was resumed for another 10 min. Finally, dialysis with phosphate buffered saline (PBS) buffer (pH 7.4) was used to remove unreacted monomers and initiators. The molar ratios of AA/AEMA/ICEMA/BACA/APEG (a/b/c/d/e) used are summarized in FIG. 2. In particular, NC-3 has an a/b/c/d/e ratio of 337/225/38/70/10. The non-bisacryloyl disulfide, BAA, was used to prepare non-biodegradable NCs.

For the preparation of the NCs conjugated with CPPs (NC-CPP), acrylated PEG-CPP (APEG-CPP) was first prepared by reacting APEG-maleimide (APEG-Mal) and CPPs (i.e., TAT-Cys) through an SH-Mal reaction in an aqueous solution at a pH of 7.4. Briefly, APEG-Mal (1.0 mg), CPPs (3.1 mg), and TCEP (1.0 mg) were dissolved in PBS (3 mL; pH 7.4). The solution was stirred at room temperature for 24 h. After dialysis against DI water for 48 h to remove impurities, the polymer, APEG-CPP, was obtained by lyophilization. Then, the NC-CPP was prepared following the similar protocol as described above with the molar ratio of AEMA/AA/ICEMA/BACA/APEG/APEG-CPP at 337/225/38/70/4/6.

Alternative method of preparing Nanocapsules, Method II. The sodium bicarbonate buffer (10 mM, pH=9.0) was freshly prepared and degassed using the freeze-pump-thaw method for 3 cycles. sNLS-Cas9-sNLS protein (Aldevron, Madison, Wis.) was combined with sgRNA (synthesized according to the manufacture's protocol, New England Biolabs, MA) at a 1:1 molar ratio and allowed to complex for 5 minutes with gentle mixing. AA, APMA, VI, and APEG were accurately weighed and dissolved in degassed sodium bicarbonate buffer (2 mg/ml). VI, APS, and TMEDA were accurately weighed and dissolved in degassed sodium bicarbonate buffer (1 mg/ml). Cas9 RNP complex was diluted to 0.12 mg/mL in sodium bicarbonate buffer in a nitrogen atmosphere. Monomer solutions were added into the above solution under stirring in the order of AA, APMA, and VI at 5-minute intervals. In each 5-minute interval, the solution was degassed by vacuum pump for 3 minutes and refluxed with nitrogen. After another 5 min, the crosslinker, BACA, was added, followed by the addition of ammonium persulfate. The mixture was degassed for 5 min, and the polymerization reaction was immediately initiated by the addition of TMEDA. After 65 min of polymerization under a nitrogen atmosphere, the APEG was added. The reaction resumed for another 30 min. Finally, dialysis with 20 mM phosphate-buffered saline (PBS) buffer (pH 7.4) was used to remove unreacted monomers and initiators. The molar ratio of AA/APMA/VI/BACA/APEG (a/b/c/d/e) used for one optimal formulation is 927/927/244/231/33.

Example 2: Characterization of RNP NCs

Figure 3:
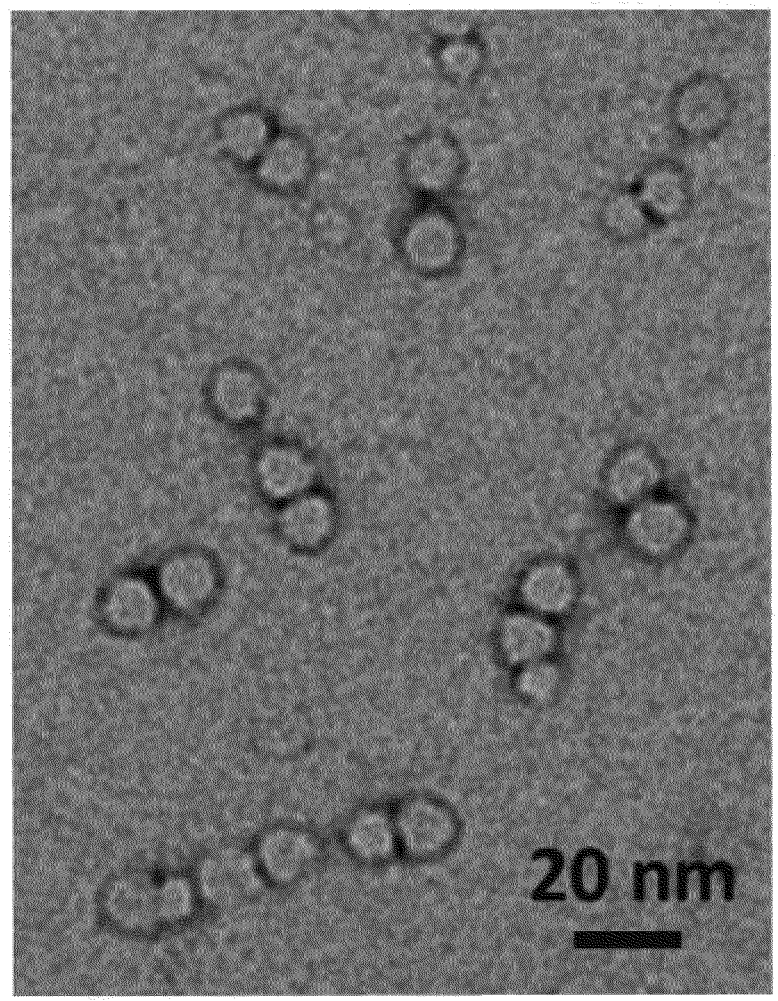
FIG. 3 shows a TEM image of an illustrative embodiment of RNP NCs. NCs were prepared using Method I at an a/b/c/d/e ratio of 337/225/38/70/10.
Figure 3:
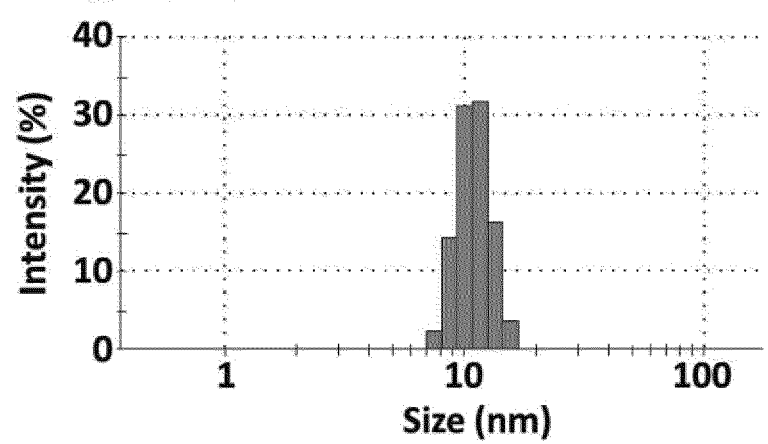

The sizes and morphologies of RNP NCs were studied by dynamic light scattering (DLS, ZetaSizer Nano ZS90, Malvern Instruments, USA) and transmission electron microscopy (TEM, FEI Tecnai $G^2$ F30 TWIN 300 KV, E.A. Fischione Instruments, Inc. USA). Zeta potentials were measured by ZetaSizer Nano ZS90 (Malvern Instruments, USA). After purification, transmission electron microscopy (TEM) of dried NC-3 indicated uniformly sized NCs with an average size of ~10 nm (FIG. 3). The average hydrodynamic diameter measured by DLS was 12.7 nm and the zeta potential of −0.9 mV was obtained for NC-3 (Table 1), indicating that the net negative charge of the RNP masked by the NC.

TABLE 1

Average hydrodynamic diameter and zeta potential of Cas9, RNP, and RNP NC (prepared by Method I).

| | Cas9 protein | RNP | RNP NC-3 |
|---|---|---|---|
| Size (nm) | 6.3 ± 0.6 | 7.6 ± 1.1 | 12.7 ± 2.8 |
| Zeta potential (mV) | 7.9 ± 3.13 | −18.5 ± 4.1 | −0.9 ± 1.3 |

Example 3: Assaying RNP Delivery and Efficacy

Cells were seeded in 96 well plates (Table 2) in 100 μL of media one day prior to transfection. On the day of transfection, RNPs with the desired guide sequence were formed, NC-RNP or Lipofectamine 2000-RNP (0.75 μL Lipofectamine 2000/well) complexes were added to the cells for transfection of RNPs. At day 6, cells were collected for flow cytometry (BD FACSCanto II) and assayed for mCherry fluorescence. Flow analysis was performed using FlowJo software.

TABLE 2

Conditions for in vitro functional testing of nanocapsules (NCs).

| Cell Type | Seeded cell number per well | Plate treatment | Cas9 dose (ng/well) |
|---|---|---|---|
| Human Embryonic Kidney (HEK) | 5000 | 0.1% Gelatin | 125 |
| Human embryonic stem cells (WA09) | 6500 | Matrigel | 350 |
| Jurkats | 5000 | N/A | 350 |
| M21 Melanoma | 5000 | 0.1% Gelatin | 250 |
| NHDF Fibroblasts | 5000 | 0.1% Gelatin | 250 |

Genomic analysis. DNA was isolated from cells using DNA QuickExtract (Epicentre, Madison, Wis.) following treatment by 0.05% trypsin-EDTA and centrifugation. QuickExtract solution was incubated at 65° C. for 15 minutes, 68° C. for 15 minutes, and finally 98° C. for 10 minutes. Genomic PCR was performed following manufacturer's instructions using Q5 High fidelity DNA polymerase (New England Biolabs) and 500 ng of genomic DNA. Products were then purified using AMPure XP magnetic bead purification kit (Beckman Coulter) and quantified using a Nanodrop2000. For deep sequencing, samples were pooled and run on an Illumina HiSeq2500 High Throughput at a run length of 2×125 bp or an Illumina Miseq 2×150 bp.

Deep sequencing data analysis. A custom python script was developed to perform sequence analysis. The pipeline starts with preprocessing, which consists of filtering out low quality sequences and finding the defined ends of the reads. For each sample, sequences with frequency of less than 100 were filtered from the data. Sequences in which the reads matched with primer and reverse complement subsequences classified as "target sequences". Target sequences were aligned with corresponding wildtype sequence using global pairwise sequence alignment. Sequences that were misaligned around the expected cut site were classified as editing events. The frequency, length, and position of matches, insertions, deletions, and mismatches were all tracked in the resulting aligned sequences.

Uptake Assay. Cells (HEKs or NHDFs) were seeded at a density of ~40,000 cells/well one day prior to transfection in 2 well culture chambers (Ibidi). NCs were formed with Atto-550 Fluorescently tagged TRACr gRNA (Integrated DNA Technologies) combined with crRNA and added to cells at 1 ug/well for transfection. Cells were imaged using an Eclipse TI epifluorescent microscope (Nikon) and as AR1 confocal microscope (Nikon) at various time-points. Image analysis was performed using CellProfiler.

Results. NCs with different formulations were tested on gene knockout efficiency using a human embryonic kidney (HEK) cell line, called the H2B-mCherry reporter system. Within each of these cells, a mCherry transgene is fused with histone 2B, so that cell nuclei are fluorescent in the red channel. By using a suitable sgRNA targeting the mCherry transgene, successful gene editing results in a loss of mCherry fluorescence in the nuclei, which is easily detectable through flow cytometry.

Figure 2:
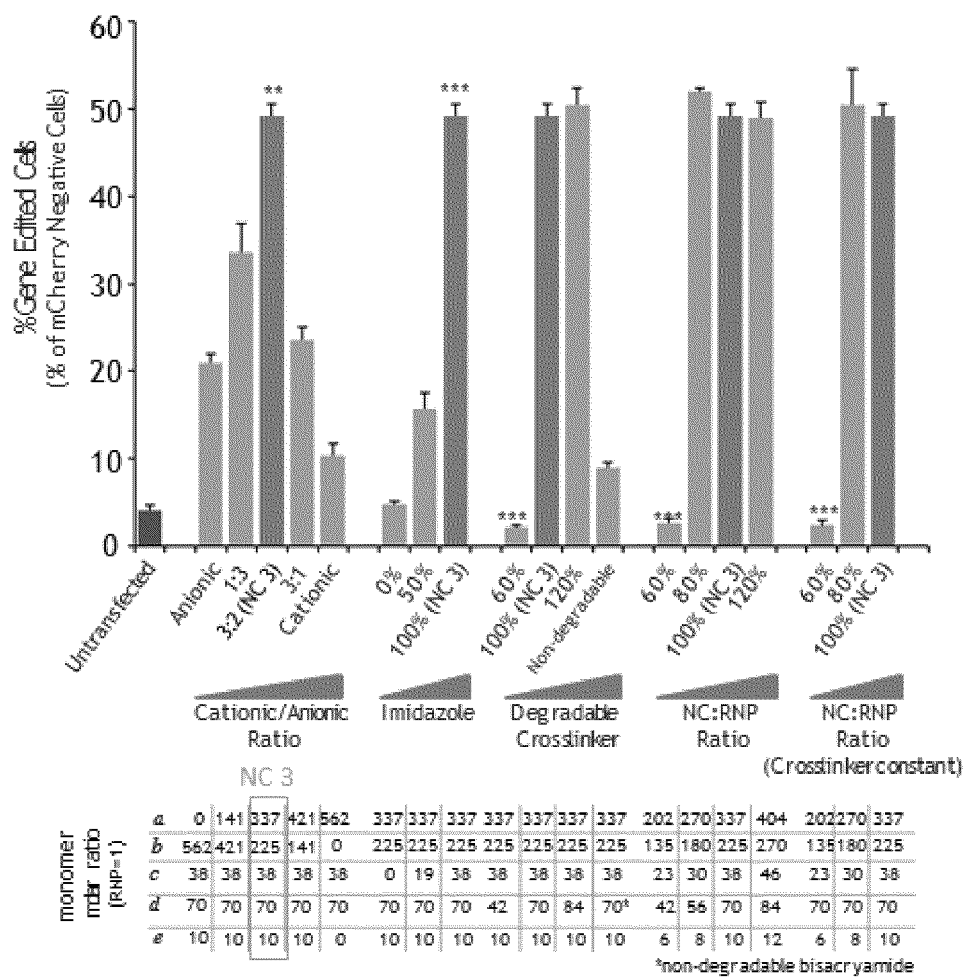
FIG. 2 shows a bar graph depicting the percent gene edited cells by various NCs in vitro using mCherry-expressing HEK 293 cells. HEK 293 cells were treated with various formulations of the RNP NCs for six days, and the loss of mCherry was measured by flow cytometry. sgRNAs within the RNPs targeted the mCherry transgene, and thus gene editing can be assayed by the loss of mCherry fluorescence within cells. Formulations investigated are listed below. NCs were prepared using Method I in the Examples.

Gene editing efficiencies for different NCs (made via Method I) are summarized in FIG. 2. Since the surface charge distribution of RNP is heterogeneous, NCs with both cationic and anionic monomers provided higher efficiencies. Pure cationic or anionic monomer formulations exhibited lower gene editing efficiencies than formulations containing both cationic and anionic monomers. The formulation containing a mixture of cationic and anionic monomers at a cationic/anionic ratio of 3:2 (NC-3) exhibited the highest gene knock-out efficacy.

Incorporation of at least some imidazolyl acryloyl monomers in NCs is helpful for high efficiency gene editing. As shown in FIG. 2, editing efficiency increased with increasing amounts of imidazolyl acryloyl monomers per NC. Crosslinker amount also affected gene editing efficiency. At a low crosslinker amount, little to no gene editing was observed, possibly due to unsuccessful formation of the NCs around RNPs. With a sufficient amount of crosslinker, similar gene editing capabilities were detected. Furthermore, NCs formed by non-bisacryloyl disulfide resulted in editing efficiencies barely above baseline, suggesting biodegradability is required to facilitate the RNP release in the cytosol. The disulfide bonds present in the degradable crosslinker can be easily cleaved in the presence of GSH in the cytosol, allowing effective release of the RNP.

Finally, the mass ratios between the NC and RNP also impacted gene editing efficiencies. A sufficient amount of acryloyl monomers to form a NC polymer coating is needed to fully encapsulate the RNP. NCs with a low NC:RNP mass ratio (e.g., NC-11) exhibited no gene editing (FIG. 2), likely due to unsuccessful NC formation through insufficient coating of RNP. Once a critical NC:RNP mass ratio was reached, similar gene editing efficiency was observed for NCs with varying NC:RNP ratios. Because unsuccessful formation of NCs can occur due to an insufficient amount of crosslinker, to decouple the effects of low NC:RNP mass ratio and crosslinker amount, two additional NC formulations were tested where NC:RNP mass ratio was changed while keeping the crosslinker amount constant. The difference in gene editing efficiencies confirmed that low total amounts of acryloyl-containing reactants can also result in unsuccessful NC formation. The NC-3 formulation made via Method I (i.e., a/b/c/d/e: 337/225/38/70/10) was selected for further study.

Shortly after transfection into human cells in vitro, the cellular uptake of NCs and cellular localization of the cargo was examined. Fluorescently-tagged gRNA was used to monitor uptake of NC-3 in neonatal human dermal fibroblasts (NHDF) and HEK cells. Both cell lines exhibited rapid uptake of NCs within 5 minutes of adding NC to the culture medium, followed by localization to the nucleus within one hour, presumably after release from NCs. After an additional five hours, there was a large increase in uptake and nuclear localization of tagged RNPs, suggesting rapid uptake of particles and disintegration of NCs to release RNP into the cytosol within this timeframe. To increase the cellular uptake of NCs, CPPB (i.e., TAT) were conjugated onto the NC. NC conjugated with the CPP (i.e., NC-CPP) displayed a higher level of cellular uptake than the NC without conjugation.

Figure 4A:
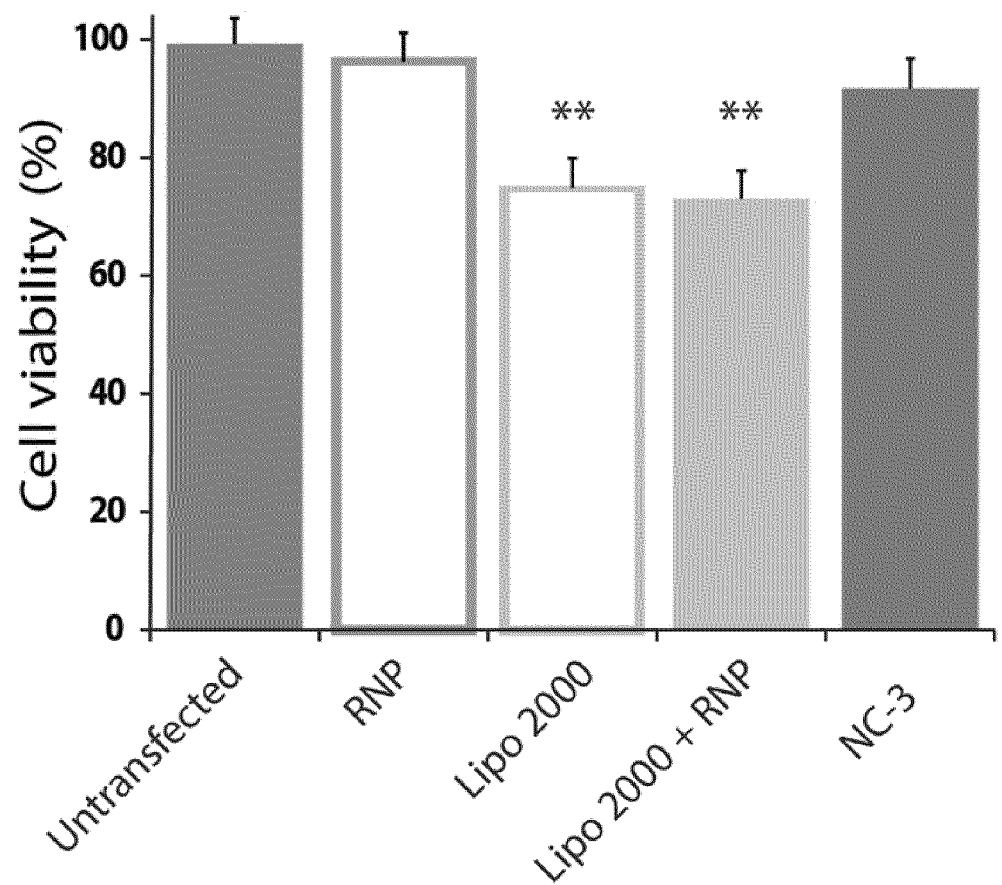
Figure 7B:
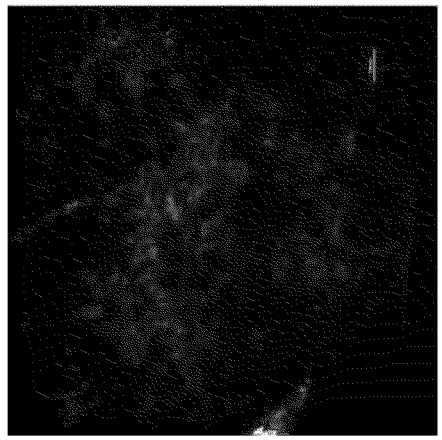
FIG. 7A-7D shows tdTomato fluorescence images of the retinal pigment epithelium from Ai14 mice. Confocal microscopy images were taken 13 days after subretinal injection of either PBS, or NC-3. NC-3 contains 8 µg of RNP and an sgRNA targeting the SV40 polyA before the tdTomato allele. NCs were prepared using Method I in the Examples with an a/b/c/d/e ratio of monomers of 337/225/38/70/10.
Figure 7D:
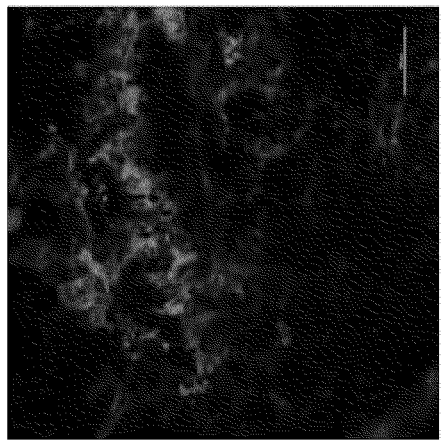
Figure 7A:
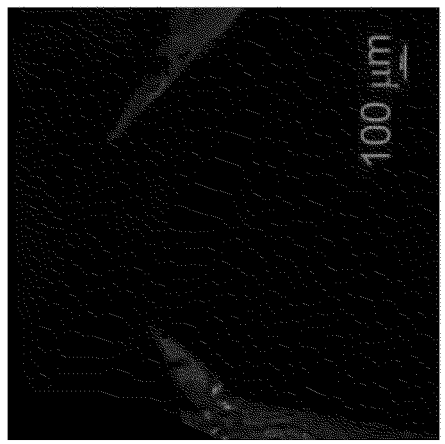
Figure 7C:
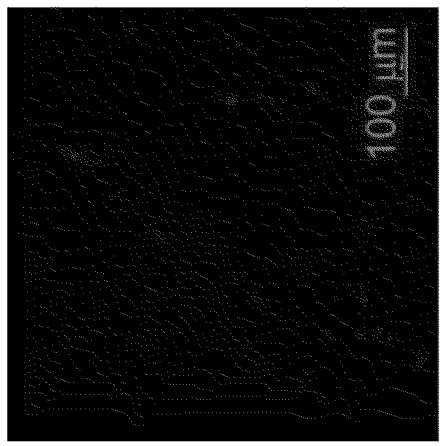

To assess effects on cell health after transfection with the NCs, we performed a colorimetric MTT assay. In this assay, a tetrazolium salt (3-[4,5-dimethylthiazol-2-yl]-2,5-diphenyl-tetrazolium bromide, MTT) is converted to a colored formazan product by enzymes active only in living cells. NC-3 did not cause significant cytotoxicity in this assay involving HEK cells (<10% cell death). Consistent with other studies, Lipofectamine 2000 exhibited significant cytotoxicity at the same dose (i.e., ~27% cell death) as shown in FIG. 4A.

NC-3 was compared in human gene editing assays with Lipofectamine 2000, the state-of-the-art commercially available transfection reagent used for Cas9 RNP delivery. As shown in FIGS. 4B and 4C, mCherry knock-out efficiency arising from gene editing within HEK cells was at least comparable, if not higher, than that of Lipofectamine 2000. NC-3 was then tested with H9 human embryonic stem cells and a Jurkat immortalized T cell line, two notable cell types where Lipofectamine 2000 has been reported to have low to no ability to deliver RNPs (X. Liang, J. Potter, S. Kumar, Y. Zou, R. Quintanilla, M. Sridharan, J. Carte, W. Chen, N. Roark, S. Ranganathan, N. Ravinder, J. D. Chesnut, *J. Biotechnol.* 2015, 208, 44.) NC-3 was able to significantly edit the H2B-mCherry transgene (FIGS. 5A-5B, 6A-6B), whereas Lipofectamine 2000 had low to no ability to produce gene edits. Embryonic stem cells were edited at a 10% efficiency using NC-3, while Jurkat cells were edited at a ~5% efficiency with NC-3 (calculated by subtracting untransfected control).

Example 4: In Vivo Evaluation of Editing Efficacy of NC-RNP

Mouse Injections.

For mice studies, Ai14 mice (obtained from Jackson Labs) were used to assay gene editing efficiency in retinal pigment epithelium (RPE). They were maintained under tightly controlled temperature (23±5° C.), humidity (40-50%) and light/dark (12/12 h) cycle conditions in 200 lux light environment. Mice were placed on a temperature-regulated heating pad, during the injection, and for recovery purposes to maintain thermal stability. Prior to the injection, the cornea was anesthetized with a drop of 0.5% proparacaine HCl and the pupil was dilated with 1% atropine. RNPs (8 μg) were formed by mixing Cas9 protein with sgRNA targeted for excision of SV40 polyA blocks (AAGTAAAACCTCTACAAATG) (SEQ ID NO: 47))at 1:1 molar ratio. (B. T. Staahl, M. Benekareddy, C. Coulon-Bainier, A. A. Banfal, S. N. Floor, J. K. Sabo, C. Urnes, G. A. Munares, A. Ghosh, J. A. Doudna, *Nat. Biotechnol.* 2017, 35, 431.) NC-3 containing RNP (8 μg) was mixed into 2.5 μL of injection volume into the sub-retinal space. Mice treated with NC-3 are expected to show tdTomato expression in the retinal pigment epithelium as a sign of successful gene editing to excise sv40 polyA blocks.

All surgical manipulations were carried out under a surgical microscope. The mice were anesthetized with ketamine (80 mg/kg) and xylazine (16 mg/kg). Injections into the sub-retinal space or the vitreous were performed using a UMP3 ultramicro pump fitted with a NanoFil syringe, and the RPE-KIT (all from World Precision Instruments, Sarasota, Fla.) and manually injected. The needle was aimed toward the inferior nasal area of the retina, and a NC-3 solution (2.5 μL) at the dose of 8 μg RNP was injected into the subretinal space. Successful administration was confirmed by bleb formation. The tip of the needle remained in the bleb for 10 s after bleb formation, when it was gently withdrawn. A solution (2.5 μL) of PBS vehicle was also injected into the subretinal space of the contra eye to serve as a control.

Imaging.

To assess tdTomato expression generated by successful gene editing, enucleated eyes from the sacrificed mice were rinsed twice with PBS, a puncture was made at ora *serrata* with a 28 gauge needle and the eyes were opened along the corneal incisions. The lens was then carefully removed. The eye cup was flattened making incisions radially to the center giving the final "starfish" appearance. The retina was then separated gently from the RPE layer. The separated RPE and retina were flat mounted on the cover-glass slide and were imaged with NIS-Elements using a Nikon C2 confocal microscope (Nikon Instruments Inc., Mellville, N.Y.). 561 nm Diode Lasers were used for red excitation and images were captured by Low Noise PMT C2 detectors in a Plan Apo VC 20×/0.75, 1 mm WD lens. We observed tdTomato expression in RPE in NC-3 injected mice but not in the controls (FIG. 7)

EQUIVALENTS

While certain embodiments have been illustrated and described, a person with ordinary skill in the art, after reading the foregoing specification, can effect changes, substitutions of equivalents and other types of alterations to the conjugates and nanoparticles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A nanocapsule comprising a single ribonucleoprotein (RNP) complex as a core and a biodegradable crosslinked polymer shell that encapsulates the core, wherein
the RNP complex comprises a Cas9 polypeptide and a guide RNA, and
the biodegradable crosslinked polymer shell comprises polymerized monomers of imidazolyl acryloyl monomers, bisacryloyl disulfides, optionally PEG acryloyl monomers, and either cationic acryloyl monomers, anionic acryloyl monomers, or both cationic and anionic acryloyl monomers, and optionally non-ionic acryloyl monomers.

2. The nanocapsule of claim 1, wherein the guide RNA is a modified guide RNA comprises
a crRNA comprising, from a single-stranded protospacer sequence, a protospacer adjacent motif for a Cas9 polypeptide, and a first complementary strand of a binding region for the Cas9 polypeptide, and
a tracrRNA comprising, a second complementary strand of the binding region for the Cas9 polypeptide,
wherein the crRNA or the tracrRNA optionally comprises an aptamer that binds a biotin-binding molecule,
wherein the crRNA and the tracrRNA hybridize through the first and second complementary strands of the binding region for the Cas9 polypeptide.

3. The nanocapsule of claim 2, wherein the crRNA and the tracrRNA form an sgRNA, the sgRNA comprising, from 5' to 3',
the single-stranded protospacer sequence,
the protospacer adjacent motif for a Cas9 polypeptide,
the first complementary strand of a binding region for the Cas9 polypeptide,
optionally, the aptamer that binds a biotin-binding molecule, and
the second complementary strand of the binding region for the Cas9 polypeptide.

4. The nanocapsule of claim 3, wherein, in the secondary structure of the modified sgRNA, the binding region for the Cas9 polypeptide and optionally the aptamer that binds the biotin-binding molecule form a stem-loop structure.

5. The nanocapsule of claim 4, wherein the modified guide RNA has the sequence (SEQ ID NO: 1)
NNNNNNNNNNNNNNNNNNNNNNNGUUUAAGAGCUAUGCUGCGAAUACGAGAUG

CGGCCGCCGACCAGAAUCAUGCAAGUGCGUAAGAUAGUCGCGGGUCGGCG

GCUCGUAUUCGCAGCAUAGCAAGUUUAAAUAAGGCUAGUCCGUUAUCAAC

UUGAAAAAGUGGCACCGAGUCGGUGCUUUU;

(SEQ ID NO: 2)
NNNNNNNNNNNNNNNNNNNNNNNGUUUAAGAGCUAUGCUGGAAACAGCAUAGC

AAGUUUAAAUAAGGCUAGUCCGUUAUCAACUUCGAAUACGAGAUGCGGCC

GCCGACCAGAAUCAUGCAAGUGCGUAAGAUAGUCGCGGGUCGGCGGCUCG

UAUUCGGAAAAAGUGGCACCGAGUCGGUGCUUUU;
or (SEQ ID NO: 3)
NNNNNNNNNNNNNNNNNNNNNNNGUUUAAGAGCUAUGCUGGAAACAGCAUAGC

AAGUUUAAAUAAGGCUAGUCCGUUAUCAACUUGAAAAAGUGGCACCGAGU

CGGUGCCGAAUACGAGAUGCGGCCGCCGACCAGAAUCAUGCAAGUGCGUA

AGAUAGUCGCGGGUCGGCGGCUCGUAUUCGUUUU.

6. The nanocapsule of claim 1 wherein the mass ratio between the polymer shell and the RNP ranges from greater than 0.4 to 10.0.

7. The nanocapsule of claim 6 wherein the mass ratio between the polymer shell and the RNP ranges from 0.4 to 3.5.

8. The nanocapsule of claim 1 wherein the polymer shell comprises polymerized monomers of both cationic and anionic acryloyl monomers.

9. The nanocapsule of claim 8 wherein the mole ratio of cationic acrylate monomers to anionic acrylate monomers ranges from 10:1 to 1:10.

10. The nanocapsule of claim 8 wherein the mole ratio of cationic acrylate monomers to anionic acrylate monomers ranges from 3:1 to 1:3.

11. The nanocapsule of claim 1 wherein the polymer shell comprises polymerized monomers of both cationic and non-ionic acryloyl monomers.

12. The nanocapsule of claim 11 wherein the mole ratio of cationic acryloyl monomers to non-ionic acryloyl monomers ranges from 10:1 to 1:10.

13. The nanocapsule of claim 11 wherein the mole ratio of cationic acryloyl monomers to non-ionic acrylate monomers ranges from 3:1 to 1:3.

14. The nanocapsule of claim 1 wherein the mole ratio of all monomers to RNP is about 400:1 to 8000:1.

15. The nanocapsule of claim 8 wherein the mole ratio of imidazolyl acryloyl monomer to RNP is 20:1 to 800:1.

16. The nanocapsule of claim 8 wherein the mole ratio of imidazolyl acryloyl monomer to RNP is 20:1 to 400:1.

17. The nanocapsule of claim 8 wherein the mole ratio of bisacryloyl disulfide monomers to RNP is 50:1 to 1000:1.

18. The nanocapsule of claim 1 where the mole ratio of PEG acryloyl monomers to RNP is 0:1 to 30:1.

19. The nanocapsule of claim 1 wherein the cationic acryloyl monomer has the structure of Formula (I):

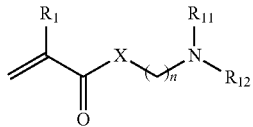

(I)

wherein
$R_1$ is H or methyl;
$R_{11}$ is H or methyl or ethyl;
$R_{12}$ is H or methyl or ethyl;
X is O or NH; and
n is 0, 1, 2, 3, 4, 5, or 6.

20. The nanocapsule of claim 19 wherein $R_{11}$ and $R_{12}$ are each H.

21. The nanocapsule of claim 1 wherein the anionic acryloyl monomer has the structure of Formula II:

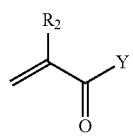

(II)

wherein
$R_2$ is H or methyl;
Y is OH, —O—$(CH_2)_m$—COOH, —O—$(CH_2)_m$—SO$_3$H, —O—$(CH_2)_m$—OPO$_3$H$_2$, —NH—$(CH_2)_m$—COOH, —NH—$(CH_2)_m$—SO$_3$H, or —NH—$(CH_2)_m$—OPO$_3$H$_2$; and
m is 1, 2, 3, 4, 5, or 6.

22. The nanocapsule of claim 1 comprising polymerized monomers of the non-ionic acryloyl monomer having the structure of Formula III:

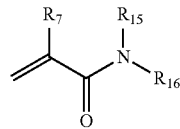

(III)

wherein
$R_7$ is H or methyl;
$R_{15}$ and $R_{16}$ are each independently H, methyl, ethyl, propyl, or isopropyl.

23. The nanocapsule of claim 1 wherein the imidazolyl acryloyl monomer has the structure of Formula IV:

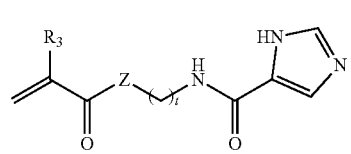

(IV)

wherein
$R_3$ is H or methyl;
Z is O or NH; and
t is 1, 2, 3, 4, 5, or 6.

24. The nanocapsule of claim 1 wherein the imidazolyl acryloyl monomer has the structure of Formula IV-2:

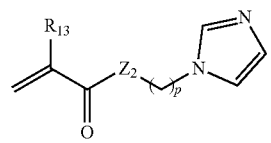

(IV-2)

wherein
$R_{13}$ is H or methyl;
$Z_2$ is O or NH; and
p is 1, 2, 3, 4, 5, or 6.

25. The nanocapsule of claim 1 wherein the imidazole monomer has the structure of Formula IV-3:

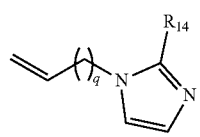

(IV-3)

wherein
$R_{14}$ is H or methyl;
q is 0, 1, 2, 3, 4, 5, or 6.

26. The nanocapsule of claim 1 wherein the bisacryloyl disulfide monomer has the structure of Formula V:

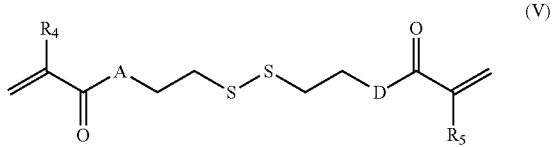

wherein
A and D are independently selected from O and NH; and
R$_4$ and R$_5$ are independently selected from H and methyl.

27. The nanocapsule of claim 1 wherein the PEG acryloyl monomer is present and has the structure of Formula VI:

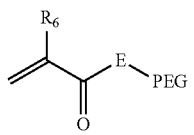

wherein
E is O or NH;
R$_6$ is H or methyl;
PEG is polyethylene glycol having a weight average molecular weight of 500 Da to 5,000 Da; and the PEG is terminated by a group selected from a targeting ligand, OH, O—(C$_{1-6}$)alkyl, NH$_2$, biotin, a cell penetrating peptide, a dye or other imaging agent.

28. The nanocapsule of claim 1 wherein at least PEG acryloyl monomer comprises a targeting ligand, a dye or a cell penetrating peptide attached to the PEG moiety.

29. A method of delivering an RNP to a cell to modify a target gene comprising exposing the cell to an effective amount of a nanocapsule of claim 1.

30. A kit comprising the nanocapsule of claim 1.

* * * * *